United States Patent [19]

Bar-Tana et al.

[11] Patent Number: 4,711,896
[45] Date of Patent: Dec. 8, 1987

[54] α, ω-DICARBOXYLIC ACIDS AND MEDICAMENTS WHICH CONTAIN THESE COMPOUNDS

[75] Inventors: Jacob Bar-Tana, Jerusalem, Israel; Ernst-Christian Witte, Mannheim, Fed. Rep. of Germany; Bernd Hagenbruch, Lampertheim, Fed. Rep. of Germany; Johannes Pill, Leimen, Fed. Rep. of Germany; Karlheinz Stegmeier, Heppenheim, Fed. Rep. of Germany

[73] Assignee: EPIS S.A., Zug, Switzerland

[21] Appl. No.: 840,563

[22] PCT Filed: Jun. 15, 1985

[86] PCT No.: PCT/EP85/00288

§ 371 Date: Feb. 21, 1986

§ 102(e) Date: Feb. 21, 1986

[87] PCT Pub. No.: WO86/00298

PCT Pub. Date: Jan. 16, 1986

[30] Foreign Application Priority Data

Jun. 22, 1984 [DE] Fed. Rep. of Germany ....... 3423166

[51] Int. Cl.$^4$ .................. A61K 31/19; C07C 121/48; C07C 121/50; C07C 57/34
[52] U.S. Cl. .................................. 514/570; 514/519; 514/520; 514/529; 514/533; 514/545; 514/574; 558/401; 558/402; 558/430; 560/81; 560/127; 562/489; 562/509
[58] Field of Search ............... 562/488, 489, 590, 595, 562/509; 560/81, 190, 127; 260/465 D; 514/520, 526, 519, 533, 545, 547, 548, 570, 574; 558/401, 402, 430

[56] References Cited

FOREIGN PATENT DOCUMENTS 1556660 11/1979 United Kingdom .

Primary Examiner—Werren B. Lone
Assistant Examiner—Vera C. Clarke
Attorney, Agent, or Firm—Felfe & Lynch

[57] ABSTRACT

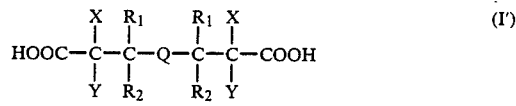

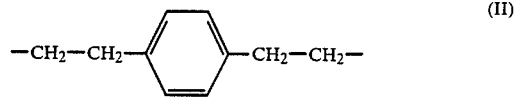

α, ω-dicarboxylic acids having the general formula (I') in which: $R_1$ and $R_2$, which may be different or the same, represent a lower alkyl group which can be substituted by hydroxy, lower alkoxy, halogen or phenyl, the phenyl being capable of substitution one or several times by hydroxy, lower alkoxy, lower alkyl or halogen; a lower alkenyl or alkinyl group; a $C_3$-$C_7$-cycloalkyl group or a phenyl group possibly substituted by hydroxy, halogen, lower alkyl or lower alkoxy, and X and Y, which may be different or the same, represent hydrogen, lower alkyl, lower alkoxy, hydroxy, cyano, halogen, carboxyl, lower alkoxycarbonyl or carbamoyl, and Q represents non-ramified, saturated or unsaturated alkyl chain with 8-14 C atoms, which can be substituted, interrupted by hetero-atoms, and form part of a cyclic system, as well as their carboxylic acid derivatives in vivo, provided that when Q represents an unramified, saturated alkyl chain with 8-14 C atoms, and $R_1$ and $R_2$ represent methyl and Y represents hydrogen, X may not represent hydrogen, ethoxy-carbonyl, bromine, cyano or methyl, and if $R_1$ and $R_2$ represent methyl and X and Y hydrogen, then Q may not represent any formula (II) group. Process for their preparation and medicines containing these compounds, which have an anti-diabetic action and lower the level of lipids.

8 Claims, No Drawings

α,ω-DICARBOXYLIC ACIDS AND MEDICAMENTS WHICH CONTAIN THESE COMPOUNDS

In EP-OS No. 0 081 930 are described some long-chained α,ω-dicarboxylic acids of the general formula I

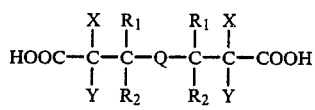

as well as in vivo hydrolysable derivatives of the carboxylic acid groups, in which $R_1$ and $R_2$ each signify an unsubstituted or substituted hydrocarbon radical or heterocycle, X and Y each signify hydrogen, optionally substituted alkyl, halogen, cyano, carboxyl, lower alkoxycarbonyl or carbamoyl, and Q a diradical which consists of a linear chain with 8 to 14 C-atoms which can be substituted by inert substituents or one or more of these C-atoms or heteroatoms can possibly form a ring.

These compounds find use as medicaments for the treatment of obesity, hyperlipidaemia or diabetes.

By way of example, there are disclosed in this Patent Application only compounds of formula I in which X signifies hydrogen, ethoxycarbonyl, bromo, cyano or methyl, Y hydrogen, $R_1$ and $R_2$ each methyl and Q a $-(CH_2)_8-$, $-(CH_2)_{10}-$ or $-(CH_2)_{12}-$ group.

It has now been found that a number of compounds which are there not disclosed and only formally fall under the broad definition of the formula I of EP-OS No. 0 081 930 display an outstanding lipid-sinking action. In addition, they show an anti-diabetic action.

Therefore, the subject of the present invention are long-chained, α,ω-dicarboxylic acids of the general formula I'

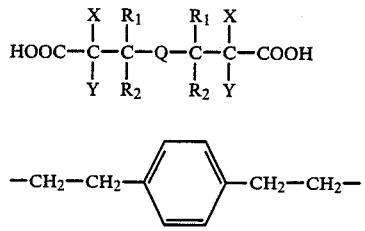

in which $R_1$ and $R_2$, which can be the same or different, signify a lower alkyl group, which can be substituted by hydroxyl, lower alkoxy, halogen or phenyl, whereby the phenyl group in turn can be substituted one or more times by hydroxyl, lower alkoxy, lower alkyl or halogen; a lower alkenyl or alkynyl group; a $C_3$-$C_7$ cycloalkyl group or a phenyl group possibly substituted by hydroxyl, halogen, lower alkyl or lower alkoxy, X and Y, which can be the same or different, signify hydrogen, lower alkyl, lower alkoxy, hydroxyl, cyano, halogen, carboxyl, lower alkoxycarbonyl or carbamoyl, and Q signifies an unbranched, saturated or unsaturated alkylene chain with 8 to 14 C-atoms which (a) can be substituted by oxygen, halogen, hydroxyl or lower alkoxy, (b) can be interrupted by one or more heteroatoms and (c) in the case of the 1-4 chain member can be component of a $C_3$-$C_7$ cycloalkyl or phenyl ring, as well as their in vivo hydrolysable carboxylic acid derivatives, with the proviso that when Q signifies an unbranched, saturated alkylene chain with 8-14 C-atoms and $R_1$ and $R_2$ are simultaneously methyl, as well as Y hydrogen, X cannot be hydrogen, ethoxycarbonyl, bromine, cyano or methyl and when $R_1$ and $R_2$ signify methyl and X and Y hydrogen, Q cannot represent a

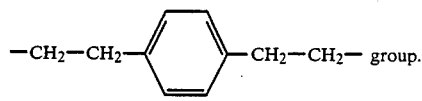 group.

The compound 1,4-phenylene-bis-(3,3-dimethyl-5-yl-pentanoic acid) is described by A. T. Blomquist et al. [Am. Soc. 80 (1958) 3405] as intermediate product without statement of a pharmacologically effectiveness.

By lower alkyl of the substituents $R_1$, $R_2$, X and Y are to be understood groups with 1-6, especially 1-4 C-atoms. The methyl and ethyl radical is preferred.

By lower alkoxy of the substituents $R_1$, $R_2$, X, Y and the alkoxy groups possibly in the radical Q are to be understood groups with 1-6, especially 1-4 C-atoms. The methoxy and ethoxy radical is preferred.

Lower alkoxycarbonyl groups of the substituents X and Y are groups with 1-6 C-Atoms. The methoxycarbonyl and ethoxycarbonyl radical is preferred.

Lower alkenyl groups of the substituents $R_1$ and $R_2$ contain 2-6 C-atoms. The allyl radical is preferred.

Lower alkynyl groups of the substituents $R_1$ and $R_2$ contain 2-6 C-atoms. The propynyl radical is preferred.

By halogen are to be understood, in all cases, fluorine, chlorine and bromine.

Lower alkyl groups substituted by phenyl are preferably the benzyl and the phenethyl radical, whereby the phenyl group can be substituted by the stated substituents.

Cycloalkyl groups $C_3$-$C_7$, such as can occur as substituents $R_1$, $R_2$ or in the partial structure of Q, are preferably cyclopropyl, —hexyl and —heptyl groups.

The group Q means, on the basis of the syntheses of the compounds of the invention, as a rule symmetrically constructed radicals. Of the linear chains, the radicals $-(CH_2)_8-$, $-(CH_2)_{10}-$, $-(CH_2)_{12}-$ and $-(CH_2)_{14}-$ are preferred.

Unsaturated chains are preferably the radicals $-(CH_2)_4-CH=CH-(CH_2)_4-$ and $-(CH_2)_5-CH=CH-(CH_2)_5-$.

The chains can be substituted by oxo oxygen, i.e. contain keto groups. The preferred radical is the group

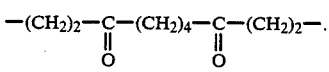

The chains can also be interrupted by heteroatoms one or more times, such as e.g. by oxygen, sulphur or optionally alkylated or benzylated nitrogen. Sulphur atoms can also be oxidised to SO or $SO_2$. Preferred radicals are: $-(CH_2)_5-O-(CH_2)_5-$; $-(CH_2)_5-S-(CH_2)_5-$;

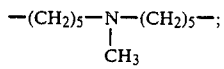

A part of the chain Q can also advantageously be part of a ring system. This ring system can be not only saturated (cycloalkylidene) but also unsaturated (phenylene). Preferred in the case of the cycloalkylidene rings are the cyclopropylidene and cyclohexylidene ring system which is incorporated into the chain in the 1,1-, 1,2-, 1,3- or 1,4-position, e.g. —(CH₂)₄13 cyclohexylidene or cyclopropylidene—(CH₂)₄—.

The number of C-atoms in the whole chain is, as a rule, uneven in the case of 1,1- and 1,3-linkage. This also applies to chains which are interrupted by 1 heteroatom.

The phenyl ring system can be incorporated into the chain via the 1,2-, 1,3- or 1,4-position, e.g. in the case of the —(CH₂)₃—phenylene—(CH₂)₃—; —(CH₂)₄—phenylene—(CH₂)₄—; —CH₂—CH=CH—phenylene—CH=CH—CH₂ or —CH₂—CH=CH—CH₂—phenylene—CH₂—CH=CH—CH₂—.

Preferred for all above-mentioned chains Q are the following meanings of the substituents $R_1$, $R_2$, X and Y: $R_1$ and $R_2$, same or different, methyl, ethyl, hydroxymethyl or phenyl, X and Y, same or different, hydrogen, halogen, methoxy, hydroxyl, ethoxycarbonyl, cyano, carbamoyl or carboxyl, but especially $R_1$ and $R_2$ in each case methyl, X and Y is each case hydrogen or Y hydrogen and X halogen, ethoxycarbonyl, hydroxyl, methoxy, cyano, carbamoyl or carboxyl.

In vivo hydrolysable derivatives of the compounds of the formula I' are e.g. salts with pharmaceutically acceptable alkali metals, alkaline earth metal or ammonium bases; esters, especially lower alkyl esters, such as methyl, ethyl and isopropyl esters; amides; mono- or dialkylated amides, such as dimethylamides; or lactones which can be formed with an OH substituent of the formula I'.

The subject of the invention are also cis/trans isomers of the unsaturated compounds.

The preparation of the compounds of formula I' takes place in per se known manner in that one
(a) converts a dihalide of the formula II

in which Hal signifies chlorine or bromine and Q has the given meaning, into a bis-Grignard compound and reacts this with 2 mole of a compound of the formula III

in which $R_1$ and $R_2$ have the given meaning, $R_3$ represents a lower alkyl group and U a COOR₃ group or a —CONH₂ or CN group, if desired saponifies the compounds obtained, if desired decarboxylates and if desired introduces the substituents alkyl, alkoxy, hydroxyl or halogen into the α- and ω-position, or for the case in which X and Y signify hydrogen, halogen, hydroxyl, alkyl or alkoxy, (b) reacts a bis-triphenylphosphonium compound of the formula IV

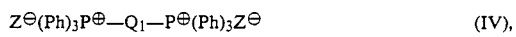

in which Z signifies chloride or bromide and $Q_1$ a straight, saturated or unsaturated alkylene chain with 2-12 C-atoms which (aa) can be substituted by oxygen, halogen, hydroxyl or lower alkoxy, (bb) can be interrupted by one or more heteroatoms and (cc) in the case of 1-4 chain members, can be part of a C₃-C₇ cycloalkyl or phenyl ring, with 2 mole of a carboxylic acid ester of the formula V

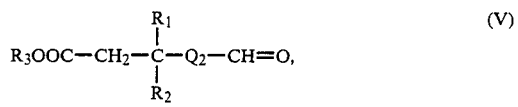

in which $R_1$, $R_2$ have the given meaning, $R_3$ signifies a lower alkyl group and $Q_2$ a valency bond or an alkylene chain with 1-5 C-atoms, with the proviso that $Q_1$ and two $Q_2$ together display not less than 8 and not more than 14 C-atoms, into the compounds obtained with X and Y=hydrogen, if desired, introduces the substituents alkyl, alkoxy, halogen and hydroxyl into the α- and ω-position, as well as, if desired, subsequently converts the esters, amides or salts obtained into free acids or converts the free acids into salts, esters or amides.

According to process (a), as a rule there are obtained tetracarboxylic acid esters. These compounds can be saponified by alkali and decarboxylated by heating to dicarboxylic acids. The compounds obtained with X, Y=hydrogen can then be halogenated in the α- and ω-position. As a rule, this takes place by fluorine, bromine or chlorine, as well as by corresponding N-succinimides. However, α- and ω-dichloro compounds can also be reacted with suitable fluorination agents, such as tetrabutyl ammonium fluoride, to the α- and ω-difluoro compounds.

The introduction of an alkyl group takes place with the corresponding alkyl halides after reaction e.g. with n-butyl lithium.

Hydroxyl group in the α- and ω-position can be introduced e.g. from corresponding dichloro compounds by alkaline saponification.

Alkoxy groups can be introduced into α- and ω-position by reaction of the corresponding dichloro compounds with alcoholates (e.g. sodium methylate).

According to process (a), dicarboxylic acids can also be obtained which carry a nitrile or carbamoyl substituents in the α- and ω-position, whereby subsequently the nitrile radical can be saponified into a carbamoyl and further to a carboxyl group or possibly a carbamoyl group can be dehydrated to a nitrile group according to usual methods.

According to process (b), one obtains compounds with X and Y=hydrogen. For this purpose, the corresponding bis-phosphonium salts of the formula IV are brought to reaction with 2 mole of a carboxylic acid ester of the formula V in the presence of strong bases, such as e.g. KOH or sodium methylate, whereby a diester results with at least doubly unsaturated radical Q. Analogously to Q, the radical $Q_1$ can be substituted, interrupted or be component of a ring system.

Instead of the bis-phosphonium salts of the formula IV, there can also be used corresponding phosphine oxides or phosphonic esters (P-O-activated olefin formation reaction).

The phenylene or cycloalkylidene compounds can also be prepared in that one reacts a compound of the formula VI

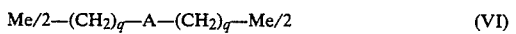

in which Me represents a divalent metal, such as e.g. cadmium or zinc, A phenylene or $C_3$-$C_7$ cycloalkylidene and q the number 1 or 2, with a compound of the formula VII

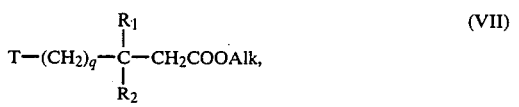

in which T represents an active carboxylic acid function, especially an acid halide or an acid anhydride group and $R_1$, $R_2$, q and Alk have the above-given meaning, saponifies the so-obtained diketodicarboxylic acid esters in the usual way and subsequently possibly reduces the keto groups.

For the olefin formation, as strong bases, there have proved useful alkali metal alcoholates, such as lithium or sodium methylate, alkali metal amides, such as sodamide, but also lithium organyls, such as e.g. butyl lithium, as well as sodium hydride. The reactions are preferably carried out in lower alcohols or in ethers, such as diethyl ether or tetrahydrofuran.

The hydrogenation of the bis-alkenes resulting according to process (b) takes place under the conditions usual for this reaction in the presence of metal catalysts, such as e.g. palladium on charcoal at normal pressure but preferably under elevated pressure and elevated temperature.

For the hydrogenation of the cyclohexane ring, platinum, rhodium or ruthenium prove to be especially suitable catalysts.

The subsequent introduction of the substituents X and Y into the α- and ω-position takes place according to the same methods as described under process (a).

For the reduction of the keto groups of the diketo acids obtainable according to process (a), there is suitable the process according to Huang-Minlon (heating of a mixture of ketone, aqueous alkali, glycol and hydrazine) or one reduces with zinc or copper-containing zinc and hydrochloric acid (Clemmensen reduction); however, one can also convert into the corresponding tosyl hydrazone and reduce this with complex boron hydrides.

The esterification of the acids according to formula I′ takes place in the usual way via the corresponding acid chloride. For this purpose, the free acid is converted with thionyl chloride into the acid chloride and this reacted with the corresponding alcohol.

The saponification of the esters obtained according to formula I′ takes place usually with alkali in alcoholic solution. It can also be carried out in acidic media with a mixture of concentrated sulphuric acid and oleum.

As pharmacologically acceptable salts, there come into question especially alkali metal, alkaline earth metal and ammonium salts.

One obtains the salts in the usual way e.g. by neutralisation of the compounds of formula I with the corresponding lyes or acids.

For the production of medicaments, the compounds of the general formula I are mixed in per se known manner with suitable pharmaceutical carrier substances, aroma, flavouring and colouring materials and formed, for example, as tablets or dragees or, with the addition of appropriate adjuvants, suspended or dissolved in water or oil, such as e.g. olive oil.

The substances of the general formula I can be administered orally or parenterally in liquid or solid form. As injection medium, water is preferably used which contains the stabilising agents, solubilising agents and/or buffers usual in the case of injection solutions. Such additives are e.g. tartrate or borate buffers, ethanol, dimethyl sulphoxide, complex formers (such as ethylenediamine-tetraacetic acid), high molecular polymers (such as liquid polyethyene oxide) for viscosity regulation or polyethylene derivatives of sorbitan anhydrides.

Solid carrier materials are e.g. starch, lactose, mannitol, methyl cellulose, talcum, highly dispersed silicic acid, high molecular polymers (such as polyethylene glycols).

Compositions suitable for oral administration can, if desired, contain flavouring and sweetening materials. For external administration, the substances I according to the invention can also be used in the form of powders and salves. For this purpose, they are mixed e.g. with powdered, physiologically acceptable dilution agents or usual salve bases.

The administered dose depends upon the age, the state of health and the weight of the recipient, the extent of the disease, the nature of simultaneously carried out further treatments, the frequency of the treatments and the nature of the desired action. The daily dose of the active compound usually amounts to 0.1 to 50 mg./kg. body weight. Normally, 0.5 to 40 and preferably 1.0 to 20 mg./kg./day in one or more application per day are effective in order to obtain the desired results.

EXPERIMENTAL REPORT

Representative for the new compounds, for the compounds of Examples 3 and 6 (b), the lipid-sinking action was determined and compared with the best compound of EP-OS No. 81 930, 3,3,14,14-tetramethylhexadecane-1,16-diacid (M 16).

For this purpose, the substance to be tested was administered, in each case, to 10 male Sprague-Dawley rats for 29 days at a dosage of 50 mg./kg./d. and 500 mg./kg./d. in methyl cellulose suspension. At the end of the experiment, 3 hours before the last probing, the cholesterol and triglyceride values in the serum were determined.

In the following Table are given the changes in % in comparison with the control collectives.

| compound mg./kg./d. | | cholesterol sinking (%) | triglyceride sinking (%) |
| --- | --- | --- | --- |
| Example 3 | 50 | 31 | 51 |
|  | 500 | 58 | 70 |
| Example 6b | 50 | 42 | 51 |
|  | 500 | 62 | 66 |
| M 16 | 50 | 24 | 42 |
|  | 500 | 38 | 55 |

Preferred in the meaning of the invention are especially the compounds set out in the following:

(1) 2,3,3,14,14,15-hexamethylhexadecane-1,16-dioic acid
(2) 2,15-dicarbamoyl-3,3,14,14-tetramethylhexadecane-1,16-dioic acid
(3) 3,14-diethyl-3,14-dimethylhexadecane-1,16-dioic acid
(4) 3,3,14,14-tetra-(prop-2-enyl)-hexadecane-1,16-dioic acid
(5) 3,3,14,14-tetracyclohexylhexadecane-1,16-dioic acid
(6) 2,15-dibromo-3,3,14,14-tetraphenylhexadecane-1,16-dioic acid
(7) 1,2-cyclopropylidene-bis-(3,3-dimethyl-7-ylheptanoic acid)
(8) 9,9-pentamethylene-3,3,15,15-tetramethylheptadecane-1,17-dioic acid
(9) 1,2-cyclohexylidene-bis-(3,3-dimethyl-7-ylheptanoic acid)
(10) 1,2-phenylene-bis-(3,3-dimethyl-7-ylheptanoic acid)
(11) 3,3,15,15-tetramethyl-9-thiaheptadecane-1,17-dioic acid
(12) 9-oxa-3,3,15,15-tetramethylheptadecane-1,17-dioic acid
(13) 9-aza-3,3,9,15,15-pentamethylheptadecane-1,17-dioic acid
(14) 3,3,14,14-tetramethyl-6,11-thiahexadecane-1,16-dioic acid
(15) 2,15-difluoro-3,3,14,14-tetramethylhexadecane-1,16-dioic acid
(16) 2,2,15,15-tetrafluoro-3,3,14,14-tetramethylhexadecane-1,16-dioic acid
(17) 2,2,15,15-tetrachloro-3,3,14,14-tetramethylhexadecane-1,16-dioic acid
(18) 2,2,15,15-tetrafluoro-3,3,14,14-tetramethylhexadecane-1,16-dioic acid
(19) 3,3,14,14-tetrahydroxymethyl-1,16-dioic acid
(20) 2,15-dichloro-3,3,14,14-tetra-(chloromethyl)-hexadecane-1,16-dioic acid
(21) 2,15-dichloro-3,3,14,14-tetra-(chloromethyl)-hexadecane-1,16-dioic acid
(22) 3,3,14,14-tetra-(4-hydroxyphenyl)-hexadecane-1,16-dioic acid
(23) 3,3,14,14-tetra-(4-chlorophenyl)-hexadecane-1,16-dioic acid
(24) 3,3,14,14-tetra-(4-methylphenyl)-hexadecane-1,16-dioic acid
(25) 3,3,14,14-tetra-(4-methoxyphenyl)-hexadecane-1,16-dioic acid The preparation of some compounds according to the invention is explained in more detail in the following Examples:

EXAMPLE 1

1,4-Phenylene-bis-[(1,1-dimethylbut-4-yl)-propane dioic acid dimethyl ester]

One drops a Grignard solution prepared from 3.3 g. magnesium turnings, 20.0 g. (62.5 mmol) 1,4-bis-(3-bromopropyl)-benzene and 150 ml. abs. tetrahydrofuran to a −20° C. cold solution of 25.6 g. (124 mmol) isopropylidenemalonic acid diethyl ester and subsequently keeps for 2-3 hours at reflux temperature. The cooled batch is poured on to acidified ice water. One separates off the aqueous phase, extracts it twice with ether, washes the combined organic phases with soda solution, dries with $Na_2SO_4$ and evaporates. The evaporation residue is heated at 0.01 bar to about 150° C. in order to remove volatile by-products, thereafter 23.6 g. (67% of theory of a viscous oil remain behind. The purification of a small amount by means of HPLC gave a viscous oil which, on DC finished plates Merck KG 60/F 254 has an Rf value of 0.8 (n-heptane-ethyl acetate 1+1) or of 0.5 (n-heptane-ethyl acetate 2+1).

NMR (DDMSO): $\delta = 1.02$ (s, 12H); 1.12 (tr. 12H); 1.40; (m, 4H); 3.30 (s, 2H); 4.07 (qu, 8H); 7.03 (m, 4H).

EXAMPLE 2

1,4-Phenylene-bis-[(1,1-dimethylbut-4-yl)-propane dioic acid

A mixture of 2.5 g (4.4 mmol) of the tetraethyl ester from Example 1, 25 ml. methanol and 1.0 g. (25 mmol) sodium hydroxide is kept for 60 hours at reflux temperature, then cooled, some water added thereto and extracted with ether. Thereafter, one acidifies, whereby the acid first precipitates out as oil. After crystallisation, one filters it off with suction, washes with water and dries. Yield 1.8 g. (90% of theory), melting point 181°–183° C. (decomp.)

NMR (DDMSO): $\delta = 1.03$ (s, 12H); 1.40–160 (m, 8H); 2.48; (m, 4H); 3.12 (s, 2H); 7.07 (s, 4H).

EXAMPLE 3

1,4-Phenylene-bis-(3,3-dimethyl-6-ylhexanoic acid) is obtained by 2 hours heating of 1,4-phenylene-bis-[(1,1-dimethylbut-4-yl)-propane-dioic acid] (Example 2) under nitrogen at 160° C.

Yield 31% of theory, melting point 119°–121° C. (cyclohexane)

NMR (DDMSO) $\delta = 0.93$ (s, 12H); 1,30 (m, 4H); 1.53; (m, 4H); 2.08 (s, 4H); 2.49, (t, 4H); 7.07 (4H).

EXAMPLE 4

1,4-Phenylene-bis-(3,3-dimethyl-6-yl-5-hexenoic acid methyl ester)

To a mixture of 6.3 g. (40 mmol) 3,3-dimethyl-5-oxopentanoic acid methyl ester, 60 ml. absolute methanol and 14.0 g. (20 mmol) 1,4-phenylene-bis-(methyltriphenylphosphonium chloride) one adds dropwise at room temperature a sodium methylate solution formed from 0.92 g. (40 mg. atom) sodium and 50 ml. absolute methanol, further stirs for three hours at room temperature and then evaporates. One dissolves the residue in methylene chloride, filters and again evaporates. After column chromatography (for the removal of a small amount of fluorescing material) by means of $CH_2Cl_2$/silica gel, one obtains 3.8 g. (49% of theory) of a colourless oil.

Isomeric mixture

NMR ($CDCl_3$): $\delta = 1.02$ (12H); 2.00–2.55 (8H); 3.58 and 3.63 (6H); 5.23–6.83 (4H); 7.27 (4H).

In analogy thereto, one obtains (a) 1,3-phenylene-bis-(3,3-dimethyl-6-yl-5-hexenoic acid methyl ester) from 3,3-dimethyl-5-oxopentanoic acid methyl ester and 1,3-phenylene-bis-(methyltriphenylphosphonium chloride).

Yield 60% of theory of oily product.

Isomeric mixture

NMR ($CDCl_3$): $\delta = 1.05$ (12H); 2.15–2.50 (8H); 3.58 and 3.67 (6H); 5.25–6.73 (4H); 7.23 (4H).

EXAMPLE 5

1,4-Phenylene-bis-(3,3-dimethyl-6-ylhexanoic acid methyl ester)

A mixture of 2.0 g. 1,4-phenylene-bis-(3,3-dimethyl-6-yl-5-hexenoic acid methyl ester), Example 4, 50 ml. ethanol and a spatula tip of 10% Pd on charcoal catalyst is hydrogenated at normal pressure in a shaking apparatus up to the ending of the hydrogen take up. After filtering off the catalyst with suction, one evaporates and obtains 1.5 g. (74% of theory) of colourless oil.

NMR (CDCl$_3$): $\delta$=0.97 (s, 12H); 1.17-1.78 (m, 8H); 2.17 (s, 4H); 2.37-2.70 (m, 4H); 3.60 (s, 4H); 7.07 (s, 4H).

In analogy thereto, one obtains (a) 1,3-phenylene-bis-(3,3-dimethyl-6-ylhexanoic acid methyl ester) by hydrogenation of 1,3-phenylene-bis-(3,3-dimethyl-6-yl-5-hexenoic acid methyl ester), (Example 4a).

Yiled: 94% of thoery, colourless oil

NMR (CDCl$_3$): $\delta$=0.98 (s, 12H); 1.10-1.93 (m, 8H); 2.20; (s, 4H); 2.38-2.73 (m, 4H); 3.63 (6H), 6.83-7.23 (m, 4H).

EXAMPLE 6

1,4-Phenylene-bis-(3,3-dimethyl-6-ylhexanoic acid)

One keeps a mixture of 0.5 g. of the methyl ester (Example 5), 5 ml. methanol and 5 ml. 2N NaOH for three hours at 90° C., distils off the methanol, adds water thereto and extracts with ether. The aqueous phase is then acidified, extracted with ether and the ether extract dried with Na$_2$SO$_4$. After the evaporation, one obtains 0.4 g. (86% of theory) of product with the melting point 120°-121° C. (cyclohexane). The product is identical with that obtained according to Example 3.

In analogy thereto, one obtains (a) 1,3-phenylene-bis-(3,3-dimethyl-6-ylhexanoic acid) by saponification of its methyl ester (Example 5a).

Yield 91% of theory, colourless oil

NMR (DDMSO): $\delta$=0.93 (s, 12H); 1.30 (m, 4H); 1.53; (m, 4H); 2.07 (s, 4H); 2.49 (t, 4H); 6.92-7.00 (m, 3H); 7.15 (t, 1H).

(b) 1,4-Phenylene-bis-3,3-dimethyl-6-yl-5-hexenoic acid) by saponification of its methyl ester (Example 4).

Yield 67% of theory, m.p. 149°-151° C. (acetone) isomeric mixture.

NMR (DDMSO): $\delta$=1.00 (3, 12H); 2.10 (s, 4H); 2.38; (m, 4H); 5.47-5.92 (m, 2H); 6.24-6.57; (m, 2H); 7.27 (m, 4H). (c) 1,3-Phenylene-bis-(3,3-dimethyl-6-yl-5-hexenoic acid) by saponification of its methyl ester (Example 4a)

Yield 91% of theory; oil, n$_D^{20}$=1.5433 isomeric mixture.

NMR (DDMSO): $\delta$=1.00 (s, 12H); 2.13 (s, 4H); 2.22-2.50; (m, 4H); 5.5-5.95 (m, 2H); 6.22-6.65; (m, 2H); 7.18 (m, 4H).

EXAMPLE 7

1,4-Cyclohexylidene-bis-(3,3-dimethyl-6-ylhexanoic acid methyl ester)

One hydrogenates in the presence of ruthenium IV oxide at 90° C. and 80 bar a mixture of 0.7 g. 1,4-phenylene-bis-(3,3-dimethyl-6-ylhexanoic acid methyl ester), Example 5, and 50 ml. methanol, filters and evaporates.

Yield 0.7 g. (98% of theory) of colourless oil..

NMR (CDCl$_3$): $\delta$=0.97 (s, 12H); 1.10-1.50 (m, 22H); 2.18 (s, 4H); 3.65 (6H) $\beta$ In analogy thereto, one obtains (a) 1,3-cyclohexylidene-bis-(3,3-dimethyl-6-ylhexanoic acid methyl ester) from the corresponding 1,3-phenylene analogue.

Yield 69% of theory of a colourless oil.

NMR (CDCl$_3$): $\delta$=0.98 (s, 12H); 1.07-1.88 (m, 22H); 2.20 (s, 4H); 3.65 (s, 6H).

EXAMPLE 8

1,4-Cyclohexylidene-bis-(3,3-dimethyl-6-ylhexanoic acid) by saponification of the methyl ester (Example 7) in analogy to Example 6.

Yield 76% of theory, melting point 167°-169° C. (ethyl acetate).

NMR (DDMSO): $\delta$=0.94 (s, 12H); 1.06-1.76 (m, 22H); 2.07 (s, 4H).

and in the same way (a) 1,3-cyclohexylidene-bis-(3,3-dimethyl-6-ylhexanoic acid) from compound of Example 7a).

Yield 89% of theory, melting point 74°-76° C. (ethyl acetate).

NMR (DDMSO): $\delta$=0.94 (s, 12H); 1.06-1.76 (m, 22H); 2.06 (s, 4H).

EXAMPLE 9

1,4-Phenylene-bis-(3,3-dimethyl-7-yl-5-heptenoic acid)

(a) 1,4-Phenylene-bis-(ethyltriphenylphosphonium bromide)

One heats a mixture of 5.84 g. (20.0 mmol) 1,4-bis-(2-bromoethyl)-benzene and 13.1 g. (50.0 mmol) triphenyl phosphine under N$_2$ atmosphere for 13 min. to 220° C., then 30 min. at 250° C.

The crude product solidified after cooling is recrystallised from ethanol: 6.6 g. (40%) of colourless crystals of the melting point 262°-263° C.

(b) 1,4-Phenylene-bis-(3,3-dimethyl-7-yl-5-heptenoic acid)

To a stirred suspension of 8.17 g. (10.0 mmol) 1,4-phenylene-bis-(ethyltriphenylphosphonium bromide) in 300 ml. water-free ether, one adds at room temperature, under N$_2$ atmosphere, 21 ml. of a 1.2M solution of n-butyl lithium in hexane, after-stirs for 15 min., then adds dropwise thereto a solution of 2.65 g. (20.0 mmol) 3,3-dimethyl-5-oxopentanoic acid methyl ester in 10 ml. ether, and subsequently heats under reflux for 2 hours.

After cooling, the precipitate is filtered off with suction, the filtrate evaporated, the oily residue taken up in 40 ml. 1N KOH and 10 ml. ethanol and heated for 2 hours at 50° C. Thereafter, one evaporates to a half, extracts several times with dichloromethane, acidifies the aqueous phase with 2N HCl and extracts this several times with dichloromethane. After drying and evaporation of the organic phase, an oil is obtained which is brought to crystallisation with ligroin: 1.0 g. (26%) of colourless crystals of the melting point 78°-80° C.

NMR (DDMSO): $\delta$=0.99 (s, 12H); 2.13 (s, 4H); 2.17 (d, J=7.2 Hz; 4H); 3.33 (d, J=6.9 Hz; 4H); 5.50-5.64 (m, 4H); 7.08 (s, 4H).

EXAMPLE 10

1,3-Phenylene-bis-(3,3-dimethyl-7-yl-5-heptenoic acid)

(a) 1,3-Phenylene-bis-(ethyltriphenylphosphonium bromide) is obtained in analogy in Example 9a) from 1,3-bis-(2-bromoethyl)-benzene and triphenyl phosphine.

Yield 42% of theory, colourless crystals, melting point 219°-220° C. (methanol).

(b) 1,3-Phenylene-bis-(3,3-dimethyl-7-yl-5-heptenoic acid) in analogy to Example 9b) with the use of 1,3-phenylene-bis-(ethyltriphenylphosphonium bromide).

Yield 51% of theory, colourless oil, n$_D^{26}$=1.5202.

Rf=0.55 (DC finished plate Merck KG 60/toluene-dioxanacetic acid 90:25:10) or 0.27 (n-heptane-ethyl acetate 1:1)

EXAMPLE 11

1,4-Phenylene-bis-(3,3-dimethyl-7-ylheptanoic acid) is obtained from 1,4-phenylene-bis-(3,3-dimethyl-7-yl-5-heptenoic acid), Example 9, by normal pressure hydrogenation with palladium as catalyst.

Yield 52% of theory, melting point 117°–119° C.

NMR (CDCl$_3$): δ=1.00 (s, 12H); 1.27–1.47 (m, 12H); 2.20 (s, 4H); 2.47–2.73 (m, 4H); 7.08 (s, 4H).

Analogously thereto, one obtains (a) 1,3-phenylene-bis-(3,3-dimethyl-7-ylheptanoic acid)

Yield 41% of theory, of colourless crystals, melting point 63°–64° C.

NMR (CDCl$_3$): =1.00 (s, 12H); 1.27–1.80 (m, 12H); 2.22 (s, 4H); 2.43–2.77 (m, 4H); 6.87–7.20 (m, 4H).

EXAMPLE 12

By hydrogenation of the corresponding 1,4-phenylene-bis acid or of the 1,3-phenylene-bis acid on a rhodium catalyst, one obtains, in analogy to Example 7:

(a) 1,4-cyclohexylidene-bis(-3,3-dimethyl-7-ylheptanoic acid)

yield: 72% of theory, colourless oil.

NMR (CDCl$_3$): δ=0.77–1.85 (m, 26H); 1.02 (s, 12); 2.22 (s, 4H).

(b) 1,3-cyclohexylidene-bis-(3,3-dimethyl-7-ylheptanoic acid)

yield: 66% of theory melting point 52°–55° C. (water)

NMR (CDCl$_3$): δ=0.80–1.80 (m, 26H); 1.02 (s, 12H); 2.23 (s, 4H).

EXAMPLE 13

1,4-Phenylene-bis-(3,3-dimethyl-5-oxo-7-ylheptanoic acid)

To 2.40 g. (0.10 g. atom) magnesium turnings one adds dropwise, with stirring, 14.6 g. (50.0 mmol) 1,4-bis-(2-bromoethyl)-benzene in 100 ml. water-free ether so that the reaction mixture boils. After ending of the addition, one refluxes for 1.5 hours, cools and introduces quickly 10.1 g. (55.0 mmol) cadmium chloride. One again refluxes for 45 min., distils off the ether and adds 100 ml. benzene to the reaction mixture. The so obtained suspension is introduced quickly and with vigorous stirring into a solution of 17.3 g. (50.0 mmol) 3,3-dimethylglutaric acid methyl ester chloride in 25 ml. benzene, refluxed for 45 min., cooled and decomposed by the addition of 2N H$_2$SO$_4$. The crude product obtained after separation, drying and evaporation of the organic phase is dissolved in 100 ml. ethanol and 100 ml. 1N KOH and heated for 3 hours at 60° C.

Subsequently, one evaporates to a half, extracts several times with ether and acidifies with 2N HCl. One now extracts the aqueous phase several times with ether, dries the combined extracts and evaporates. The oil remaining behind is triturated with ligroin/ether to bring about crystallisation: 4.1 g. (20%) colourless crystals of the melting point 116°–120° C. (isopropanol).

NMR (CDCl$_3$): δ=1.06 (s, 12H); 2.55 (s, broad; 8H); 2.50–3.00 (m, 8H); 7.03 (s, 4H).

EXAMPLE 14

1,4-Phenylene-bis-(3,3-dimethyl-7-ylheptanoic acid)

One heats a mixture of 1.05 g. (2.50 mmol) 1,4-phenylene-bis-(3,3-dimethyl-5-oxo-7-ylheptanoic acid), Example 13, 1.00 g. (17.0 mmol) potassium hydroxide and 1.03 g. (20.0 mmol) hydrazine hydrate in 10 ml. diethylene glycol for 2 hours under reflux, then for 5 hours at 200° C., whereby one distils off the water. Subsequently, one cools, pours into 70 ml. water and acidifies with dilute hydrochloric acid. One after-stirs for 1 hour and collects the separated precipitate: 0.60 g. (61%) colourless crystals of the melting point 118°–120° C. (toluene).

The compound is identical with that obtained according to Example 11.

EXAMPLE 15

2,15-Dichloro-3,3,14,14-tetramethylhexadecane-1,16-dioic acid 0.128 g. 3,3,14,14-tetramethylhexadecane-1,16-dioic acid, prepared according to Example 4 of EP-OS No.0 081 930, is dissolved in 2 ml. SOCl$_2$. The mixture is boiled under reflux for 2 hours and subsequently 2 ml. SOCl$_2$ and 0.162 g. N-chlorosuccinimide (NCS) added thereto. The mixture is boiled under reflux for a further 4.5 hours, evaporated in dryness and the crude product dissolved in CCl$_4$ and filtered off. The filtrate is evaporated to dryness and the crude bis-(alpha-chloro acid chloride) is applied to a silica gel column and eluted with petroleum ether.

Yield: 84%

NMR (CDCl$_3$): 4.46 (s, 2H); 1.34 (m, 20H); 1.00 (s, 6H); 0.97 (s, 6H).

The bis-(alpha-chloro acid chloride) is quantitatively hydrolysed with water by 16 hours boiling. The reaction mixture is then extracted with chloroform and the chloroform extract dried over anhydrous magnesium sulphate, filtered and evaporated in dryness. The crude product is dissolved in bicarbonate solution, acidified to pH 2.0 and extracted with chloroform. The chloroform extract is dried over anhydrous magnesium sulphate, evaporated to dryness and further dried for 24 hours in a high vacuum. The solid product is recrystallised with petroleum ether.

Melting point 103°–112° C.

NMR (CDCl$_3$): 4.17 (s, 2H); 1.26 (m, 20H); 1.00 (s, 12H).

Analysis: %C 58.12 (calc. 58.38); %H 8.70 (calc. 8.82).

EXAMPLE 16

2,15-Dihydroxy-3,3,14-,14-tetramethylhexadecane-1,16-dioic acid 0.2 g. 2,15-Dichloro-3,3,14,14-tetramethylhexadecane-1,16-dioic acid, prepared according to Example 15, is dissolved in 10 ml, 30% KOH solution. The mixture is boiled for 3 hours, cooled and acidified to pH 2.0. The residue is filtered off and dissolved in ethyl acetate. Upon the addition of petroleum ether, a solid product crystallises out.

Melting point 87°–100° C. Yield 61%.

NMR (CDCl$_3$): 3.90 (s, 2H); 1,18 (m, 20H); 0.90 (s, 12H).

Analysis: %C 64.24 (calc. 64.17); %H 10.15 (calc. 10.16).

EXAMPLE 17

1,14-Di-(carbomethoxy)-1,14-dichloro-2,2,13,13-tetramethyltetradecane 1.28 g. 2,15-Dichloro-3,3,14,14-tetramethylhexadecane-1,16-dioic acid chloride, prepared according to Example 15, was dissolved in 50 ml. absolute methanol. The mixture was boiled under reflux for 16 hours, thereafter evaporated to dryness and the crude product dissolved in chloroform. The chloroform phase was washed with bicarbonate solution and water, dried over anhydrous magnesium sulphate and evaporated to dryness.

Yield: 40%

NMR (CDCl$_3$): 4.15 (s, 2H); 3.70 (s, 6H); 1.20 (m, 20H); 1.05 (s, 12H).

EXAMPLE 18

2,15-Dimethoxy-3,3,14,14-tetramethylhexadecane-1,16-dioic acid 1.21 g. 2,15-Dibromo-3,3,14-,14-tetramethylhexadecane-1,16-dioic acid, prepared according to Example 9 of EP-OS No. 0 081 930, was dissolved in 50 ml. methanol, in which are contained 0.58 g. sodium methylate. Thereafter, 64 ml. water were added thereto and the mixture heated to 60° C. for 4 days. The solvent was evaporated to dryness and the crude product dissolved in water, washed with ether, acidified with HCl and extracted with ether. The ether extract was dried over anhydrous magnesium sulphate and evaporated to dryness.

Yield: 61%.

NMR (CDCl$_3$): 3.47 (s, 2H); 3.39 (s, 6H); 1.24 (m, 20H); 0.95 (d, 12H).

IR: 3000, 1712, 1120 cm$^{-1}$

Analysis: %C 65.51 (calc. 65.67); %H 10.60 (calc. 10.45).

EXAMPLE 19

3,3,14,14-Tetramethyl-8-hexadecene-1,16-dioic acid 40.0 g. Dimedone were dissolved in 60 ml. 20% KOH solution and subsequently 33.0 g. 1,4-dibromobut-2-ene, 1.4 g. copper powder, which had been obtained by reduction of CuO, and 14 ml. 20% KOH solution added thereto. The mixture was stirred for 4 days and the solid product dissolved in 10% NaOH. The basic solution was filtered off, the filtrate extracted with ether and acidified, whereby the 1,4-bis-dimedone-but-2-ene condensation product precipitated out. 1,4-bis-dimedone-2-but-ene was recrystallised from acetone.

Melting point 205°-206° C.

NMR (DMSO): 5.20 (m, 2H); 2.72 (m, 4H); 2.20 (s, 8H); 1.025 (s, 6H).

Analysis: %C 72.29 (calc. 72.12); %H 8.43 (calc. 8.69).

Mass spectrum: molecular ion-332.

8.0 g. 1,4-bis-dimedone-but-2-ene, 6 ml. 85% hydrazine hydrate and 5 ml. methanol were added to a solution of 5.0 g. NaOH in 50 ml. triethylene glycol. The mixture was heated for 36 hours at 120° C., thereafter heated to 195° C. in order to evaporate water and subsequently boiled under reflux for 20 hours. The mixture was cooled, diluted with water, extracted with ether, acidified and extracted with methylene chloride. The methylene chloride extract was washed with water, dried over anhydrous magnesium sulphate, evaporated to dryness and, for further purification, applied to a silica gel column. Elution with methylene chloride/methanol (20:1) gives the title compound, which was recrystallised from petroleum ether.

Melting point 100°-101° C.

NMR (CDCl$_3$): 5.38 (quint. 2H); 1.99 (q, 4H); 1.31 (m, 12H); 1.01 (s, 12H).

Analysis: %C 70.54 (calc. 70.59); %H 10.78 (calc. 10.59).

EXAMPLE 20

3,3,14,14-Tetraphenyl-6,11-diketohexadecane-1,16-dioic acid

To a suspension of 2.0 g. 4,4-diphenylcyclohexanone (J. Org. Chem., 28, 2544, (1968) in 20 ml. absolute THF was added dropwise the Grignard compound which had been prepared from 0.49 g. 1,4-dibromobutane and 0.7 g. magnesium tirnings in 15 ml. absolute THF, while stirring. The reaction mixture was boiled under reflux for 16 hours, cooled, poured into a mixture of hydrochloric acid and ice, thereafter diluted with water and subsequently extracted with diethyl ether. The ether extract was washed with water, dried over anhydrous magnesium sulphate and evaporated to dryness. One obtains 1,4-bis-(4,4-diphenyl-1-cyclohexanol)-butane.

NMR (CDCl$_3$): 7.08–7.36 (m, 20H); 2.38 (m, 8H); 1.55 (m, 8H); 1.23 (m, 8H).

0.5 g. 1,4-Bis-(4,4-diphenyl-1-cyclohexanol)-butane was dissolved in 40 ml. acetic acid and subsequently 3.0 g. CrO$_3$ added portionwise thereto. The mixture was maintained for 16 hours at room temperature, poured on to ice and subsequently extracted with ether. The ether extract was extracted with sodium carbonate solution. The aqueous phase was acidified, extracted with ether. The ether extract was dried over anhydrous magnesium sulphate and evaporated to dryness.

Yield: 50%

NMR (CDCl$_3$): 9.90 (br. s, 2H); 7.13 (m, 20H); 1.9–3.0 (m, 20H).

EXAMPLE 21

3,3,14,14-Tetraphenylhexadecane-1,16-dioic acid 0.27 g. 3,3,14,14-Tetraphenyl-6,11-diketohexadecane-1,16-dioic acid, prepared according to Example 23, and 0.23 g. 85% hydrazine hydrate were added to a solution of 0.4 g. KOH in 10 ml. triethylene glycol. The mixture was heated for 24 hours at 120° C., subsequently heated to 195° C. in order to evaporate the water and then boiled under reflux for 7 hours. The mixture was cooled, diluted with water, extracted with ether, acidified and extracted with ether. The ether extract was washed with water, dried over anhydrous magnesium sulphate and evaporated to dryness.

Yield: 58%

NMR (CDCl$_3$): 9.7 (s, 2H); 7.16 (m, 20H); 3.05 (s, 4H); 1.2–2.6 (m, 20H).

IR: 3050; 1700 cm$^{-1}$.

EXAMPLE 22

2,15-Difluoro-3,3,14,14-tetramethyl-1,16-hexadecane dioic acid

A mixture of 9.2 g. (29 mmol) tetrabutylammonium fluoride and 3.4 g. (6.4 mmol) 2,15-dibromo-3,3,14,14-tetramethyl-1,6-hexadecane-dioic acid was stirred for 48 hours at 60° C. After the addition of water and extraction of the organic material with dichloromethane, one washes the organic solution with water, dries over magnesium sulphate and evaporates. The evaporation residue is dissolved in 50 ml, absolute methanol which contains 0.6 ml. conc. sulphuric acid. One now keeps the mixture for 16 hours at reflux temperature. Removal of the methanol in vacuum and neutralisation with 5% aqueous sodium bicarbonate solution yields 2.0 g. of crude dimethyl ester which is purified by column chromatography on silica gel (10% ether plus 90% hexane as eluent).

NMR (CDCl$_3$): δ=0.959 (d, 6H); 0.957 (d, 6H); 1.294 (m, 20H); 3.776 (s, 6H); 4.615 (d, 2H, $J_{H-F}$=43.8 Hz).

A mixture of 2.5 g. (7.9 mmol) tetrabutylammonium fluoride trihydrate and 120 mg. (0.296 mmol) of the diester is stirred under argon for 16 hours at 60° C. One now adds water thereto, extracts the organic material with ether, dries the organic solution with magnesium sulphate and removes the solvent in a vacuum. The colourless material remaining behind is recrystallised twice from hexane which contains a small amount of dichloromethane.

Yield: 42 mg. (38% of theory) of colourless dicarboxylic acid, melting point: 96°-98° C.

NMR (CDCl$_3$): δ=1.024 (s, 6H); 1.031 (s, 6H); 1.251 (m, 20H); 4.643 (d, 2H, $J_{H-F}$=48.6 Hz); 7.350 (s, br, 2H).

EXAMPLE 23

2,15-Dichloro-3,3,14,14-tetramethylhexadecane-1,16-dioic acid diisopropyl ester

The preparation of 2,15-dichloro-3,3,14,14-tetramethylhexadecane-1,16-dioic acid dichloride by chlorination by means of thionyl chloride and α-chlorination by means of N-chlorosuccinimide from the corresponding acid was so carried out exactly as described in Example 15. The isopropyl ester is prepared in that one mixes a solution of the acid chloride in carbon tetrachloride at 0° C. with isopropanol, the reaction mixture is stirred for 48 hours at room temperature and finally evaporated. The evaporation residue is taken up in chloroform, washed with water, aqueous sodium bicarbonate solution and water and dried with sodium sulphate. After evaporation of the solvent, one purifies by flash chromatography (silica gel with a gradient of methylene chloride in hexane).

Yield: 69% of theory, as well as about 20% of trichloro derivative.

NMR (CDCl$_3$): δ=1.01 (s, 12H); 1.22 (s, b, 20H); 1.26 (d, 12H); 4.18 (s, 2H); 5.01 (septet, 2H).

EXAMPLE 24

2,2,15,15-Tetrachloro-3,3,14,14-tetramethylhexadecane-1,16-dioic acid

To a solution of 0.612 g. (6.1 mmol) dry diisopropylamine in 20 ml. dry THF, one slowly adds at ice temperature under nitrogen a solution of n-butyl lithium in hexane (4,489 ml., 6.1 mmol). One stirs for a further 30 minutes at ice bath temperature, then cools to −78° C. and slowly adds dropwise thereto a solution of 1.5 g. (3.03 mmol) 2,15-dichloro-3,3,14,14-tetramethylhexadecane-1,16-dioic acid diisopropyl ester in 15 ml. anhydrous THF. One now stirs for 30 minutes at −78° C. and then adds dropwise thereto 3.0 ml. dry carbon tetrachloride, whereby the yellow colour changes to brown. One allows the reaction mixture to warm slowly and leaves to stand overnight at room temperature. It is then cooled to 0° C. and a 3N HCl solution added thereto to pH 1. One distils off the THF in a vacuum, adds methylene chloride and water thereto and washes the organic phase with water and aqueous bicarbonate solution. After drying with sodium sulphate and evaporation of the solvent, one purifies the crude product by flash chromatography on silica gel with a methylene chloride gradient in hexane as eluent.

Yield: 57% of theory tetrachloroisopropyl ester as colourless oil.

NMR (CDCl$_3$): δ=1.18 (s, b, 20H); 1.23 (s, 18H); 1.35 (s, 6H); 5.03 (septet, 2H).

For the preparation of the title compound, one drops an ice-cold mixture of equal parts by weight of concentrated sulphuric acid and oleum, with external cooling, to pulverised diester, stirs at ice-bath temperature for 10 minutes and possibly adds further sulphuric acid-oleum mixture thereto so that the diester is completely dissolved. The reaction mixture is then cooled to −78° C. and a mixture of ice and methylene chloride added thereto. After the melting of the ice, one separates the layers, extracts the aqueous phase with methylene chloride and dries the combined organic phases with sodium sulphate. Evaporation of the solvent gives the title compound in a yield of 78% of theory, m.p. 154°-154.5° C. (from cyclohexane).

We claim:

1. An α,ω-dicarboxylic acid compound of formula I′

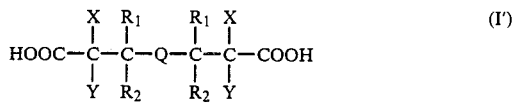

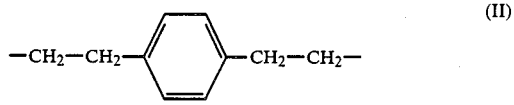

in which R$_1$ and R$_2$, which can be the same or different, signify a C$_1$-C$_6$ lower alkyl group, which is unsubstituted or is substituted by hydroxyl, C$_1$-C$_6$ lower alkoxy, halogen, phenyl or phenyl substituted one or more times by hydroxyl, C$_1$-C$_6$ lower alkoxy, C$_1$-C$_6$ lower alkyl or halogen, a C$_2$-C$_6$ lower alkenyl or C$_2$-C$_6$ alkynyl group; a C$_3$-C$_7$ cycloalkyl group, a phenyl group, or a phenyl group substituted by hydroxyl, halogen, C$_1$-C$_6$ lower alkyl or C$_1$-C$_6$ lower alkoxy, X and Y, which can be the same or different, signify hydrogen, C$_1$-C$_6$ lower alkyl, C$_1$-C$_6$ lower alkoxy, hydroxyl, cyano, halogen, carboxyl, C$_1$-C$_6$ lower alkoxycarbonyl or carbamoyl, and Q represents a —(CH$_2$)$_n$—cyclohexylidene—(CH$_2$)$_n$—, a —(CH$_2$)$_m$—phenylene—(CH$_2$)$_m$—, a —CH$_2$—CH=CH—phenylene—CH=CH—CH$_2$— or a —CH$_2$—CH=CH—CH$_2$—phenylene—CH$_2$—CH=CH—CH$_2$—group, n is 2, 3 or 4 and m is 3 or 4, or an in vivo hydrolysable carboxylic acid derivative thereof.

2. The compound of claim 1, wherein R$_1$ and R$_2$ are the same or different and are methyl, ethyl, hydroxymethyl or phenyl, and X and Y are the same or different and are hydrogen, halogen, methoxy, hydroxyl, cyano, ethoxycarbonyl, carbamoyl or carboxyl.

3. The compound of claim 1 wherein R$_1$ and R$_2$ are each methyl, Y is hydrogen and X is hydrogen, halogen, methoxy, hydroxyl, cyano, ethoxycarbonyl, carbamoyl or carboxyl.

4. The compound of claim 1 wherein R$_1$ and R$_2$ are each methyl, and X and Y are each hydrogen.

5. The compound of claim 1 designated 1,4-Phenylene-bis-(3,3-dimethyl-6-yl-hexanoic acid) or 1,4-phenylene-bis-(3,3-dimethyl-6-yl-hex-5-enoic acid).

6. The compound of claim 1 wherein the in vivo hydrolysable carboxylic acid derivative is a salt with a pharmacologically acceptable alkali metal, alkaline earth metal or ammonium base, an ester with a lower alcohol, an amide with ammonia or lower alkylamine or a lactone.

7. A pharmaceutical composition comprising a lipid sinking or antidiabetic effective amount of the compound of claim 1 in admixture with usual carrier and adjuvant materials.

8. A pharmaceutical composition comprising a lipid sinking or antidiabetic effective amount of a compound selected from the group consisting of 1,4-phenylene-bis-(3,3-dimethyl-6-yl-hexanoic acid) and 1,4-phenylene-bis-(3,3-dimethyl-6-yl-hex-5-enoic acid).

* * * * *

UNITED STATES PATENT AND TRADEMARK OFFICE
CERTIFICATE OF CORRECTION

PATENT NO. : 4,711,896

DATED : December 8, 1987

INVENTOR(S) : Bar-Tana, Jacob, et al.

It is certified that error appears in the above-identified patent and that said Letters Patent is hereby corrected as shown below:

Column 1, lines 46-49:  delete

"  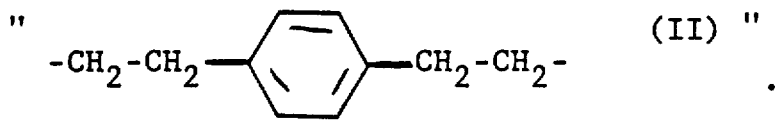  (II) "

Column 3, line 13:  delete "-$(CH_2)_4$13 cyclohexyli-"
and insert -- -$(CH_2)_4$-cyclohexyli- --.

Column 8, line 12:  after "dioc acid" insert -- ] --.

Column 14, line 10:  after "(1968)" insert -- ) --.

Column 16, lines 26-29,
Claim 1:  delete

"  (II)  "

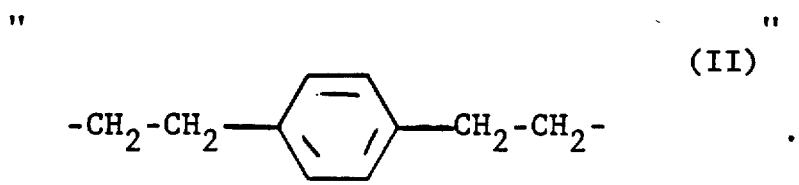

Signed and Sealed this

Twentieth Day of December, 1988

Attest:

DONALD J. QUIGG

Attesting Officer   Commissioner of Patents and Trademarks